(12) United States Patent
deCorral

(10) Patent No.: US 8,323,575 B2
(45) Date of Patent: Dec. 4, 2012

(54) VISUALIZATION OF CHEMICAL-ANALYSIS DATA

(75) Inventor: Jose Luis deCorral, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 798 days.

(21) Appl. No.: 11/913,836

(22) PCT Filed: May 12, 2006

(86) PCT No.: PCT/US2006/018637
§ 371 (c)(1),
(2), (4) Date: Nov. 20, 2008

(87) PCT Pub. No.: WO2006/124724
PCT Pub. Date: Nov. 23, 2006

(65) Prior Publication Data
US 2009/0175766 A1 Jul. 9, 2009

Related U.S. Application Data

(60) Provisional application No. 60/680,402, filed on May 12, 2005.

(51) Int. Cl.
*G01N 30/02* (2006.01)
*G01N 35/00* (2006.01)
*G06F 17/00* (2006.01)
*G06T 1/00* (2006.01)
*G06T 11/20* (2006.01)
*B01D 59/44* (2006.01)
*H01J 49/00* (2006.01)

(52) U.S. Cl. .............. 422/89; 422/70; 436/43; 345/418; 345/440; 250/282

(58) Field of Classification Search .................... 703/21; 436/50; 422/70, 89; 250/282
See application file for complete search history.

(56) References Cited

U.S. PATENT DOCUMENTS

| | | | | |
|---|---|---|---|---|
| 5,240,616 | A * | 8/1993 | Kato et al. | 210/656 |
| 7,365,311 | B1 * | 4/2008 | Cetto | 250/282 |
| 7,606,667 | B2 * | 10/2009 | Herold et al. | 702/22 |

(Continued)

FOREIGN PATENT DOCUMENTS

JP 2000-299083 10/2000
(Continued)

OTHER PUBLICATIONS de Corral, Jose' et al. "Hardware-Accelerated 3D Visualization of Mass Spectrometry Data," IEEE Visualization, 2005, p. 439-446.*
Wolkenstein, M. G. et al. "New software tools for visualization of analytical data," Fresenius J. Anal. Chem. 1998, 361: 722-724.*

(Continued)

*Primary Examiner* — In Suk Bullock
*Assistant Examiner* — Bryan Kilpatrick
(74) *Attorney, Agent, or Firm* — Muirhead and Saturnelli, LLC

(57) ABSTRACT

A method includes compressing chemical-analysis data points with no loss of information, generating, from the stored data points, nested data arrays, storing the nested data arrays in a video memory, rendering an image from the nested data arrays, and displaying the rendered image. A chemical-analysis instrument includes a chromatography module, a mass-spectrometry module that receives an eluent from the chromatography module, a computer unit that receives data points from the chromatography and mass-spectrometry modules, and a monitor for displaying rendered images.

20 Claims, 15 Drawing Sheets

U.S. PATENT DOCUMENTS

| | | |
|---|---|---|
| 2004/0080536 A1 | 4/2004 | Yakhini et al. |
| 2004/0195500 A1* | 10/2004 | Sachs et al. .................. 250/282 |
| 2005/0253843 A1 | 11/2005 | Petterson et al. |

FOREIGN PATENT DOCUMENTS

| | | | |
|---|---|---|---|
| WO | WO-03012543 | * | 12/2003 |
| WO | WO 2004/090526 A1 | | 10/2004 |
| WO | WO 2005/015209 A2 | | 2/2005 |

OTHER PUBLICATIONS

Frank Losasso and Hugues Hoppe; Geometry Clipmaps: Terrain Rendering Using Nested Regular Grids; SIGGRAPH 2004, 769-776.

Japanese Office Action dated Aug. 30, 2011 for a counterpart Japanese application.

Japanese Application No. 2008-511450, Office Action dated Aug. 30, 2011 with English Translation.

\* cited by examiner

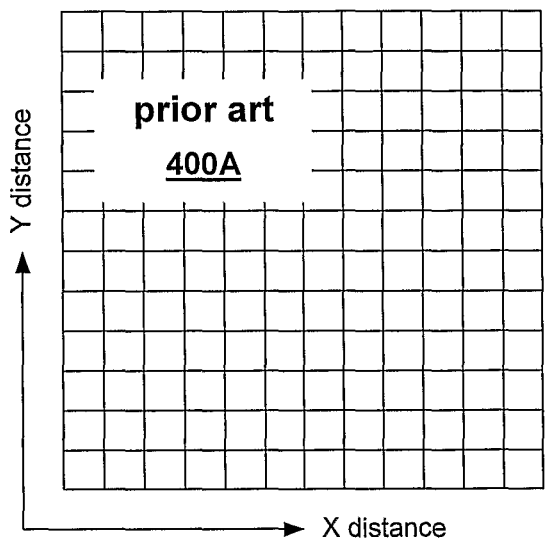
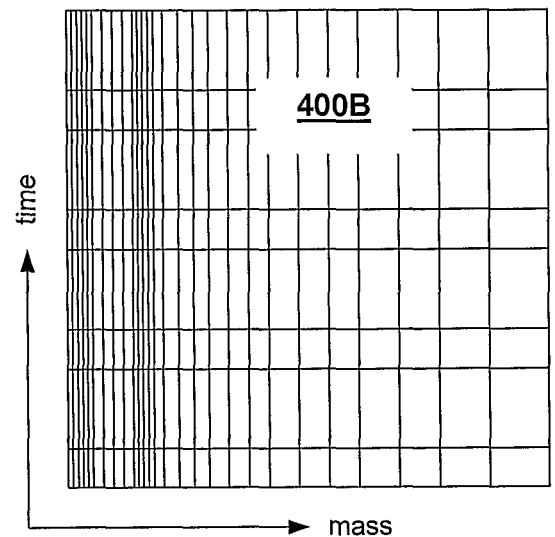
FIG. 4A  FIG. 4B
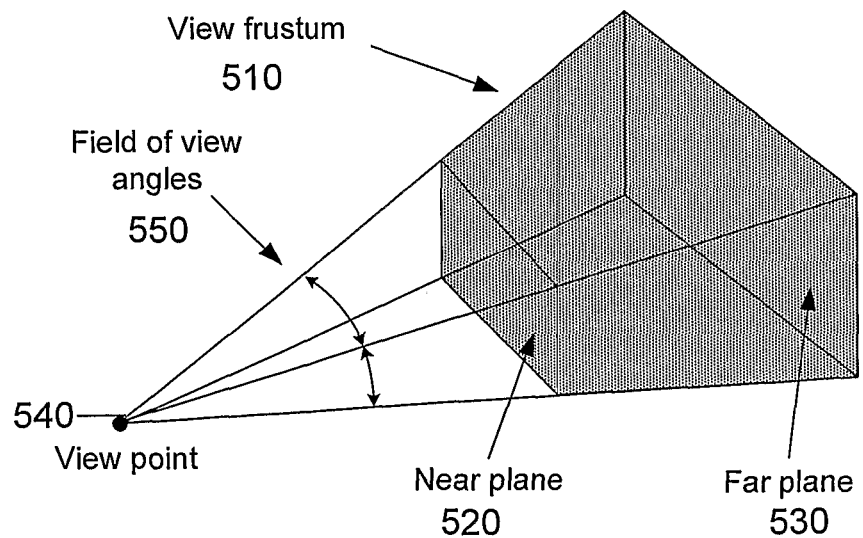
FIG. 5

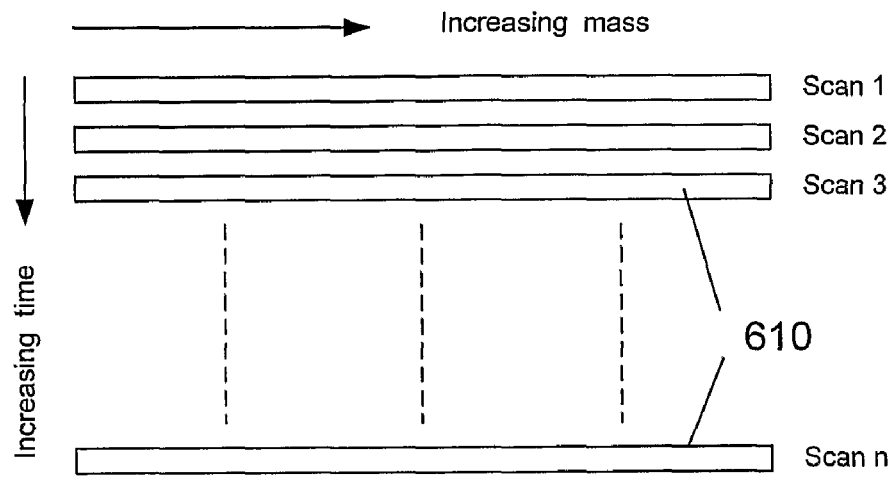
FIG. 6
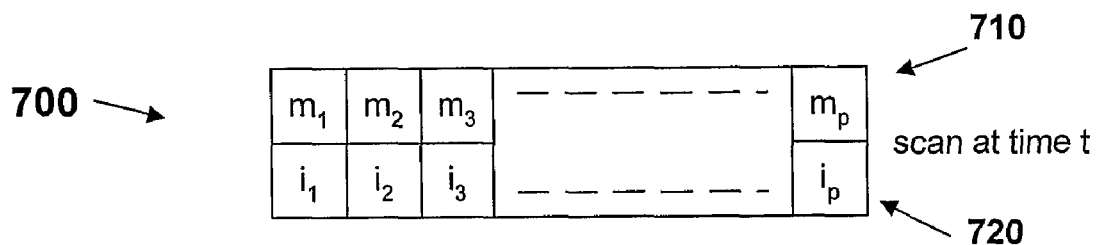
FIG. 7
FIG. 8

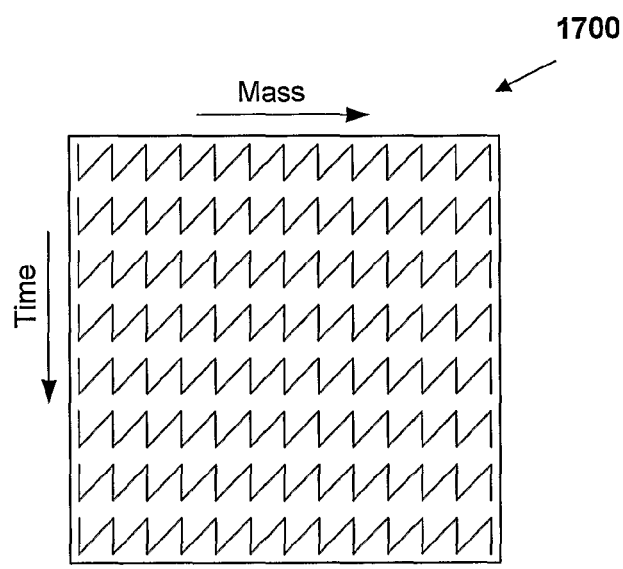
FIG. 17
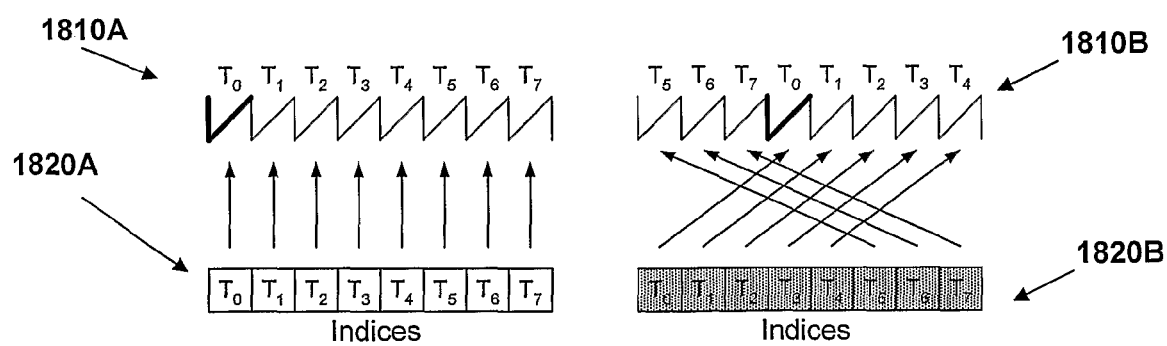
FIG. 18A
FIG. 18B

VISUALIZATION OF CHEMICAL-ANALYSIS DATA

RELATED APPLICATIONS

This application claims priority to and benefit of U.S. Provisional Patent Application No. 60/680,402, filed May 12, 2005, the entire contents of which is incorporated herein by reference.

TECHNICAL FIELD

The invention relates generally to chemical analyses of compounds, and, more particularly, to methods and apparatus for displaying data derived from chemical analyses.

BACKGROUND INFORMATION

A demand for faster and more accurate chemical analyses has motivated development of several analytical techniques. Two such techniques are Liquid Chromatography (LC) and Mass Spectrometry (MS).

FIG. 1 is an example of a typical LC chromatogram obtained through use of an Ultraviolet (UV) absorption detector. The chromatogram includes several peaks associated with different sample compounds. The duration of a LC analysis, also known as a run, typically requires a few minutes to a few hours or more, depending on the type of sample. Most LC detectors provide an item of information, such as an intensity value, per selected unit of time. The collected information provides a two-dimensional (2-D) graph—a chromatogram—of detector-measured intensity versus retention time. Peaks in the graph indicate the presence of separated sample compounds.

In contrast to LC, MS provides mass-related information for sample compounds. Prior to mass analysis, sample compounds are ionized and often fragmented. A MS instrument uses electric and/or magnetic fields to accelerate ions and direct them to an ion detector. In some MS instruments, fields are swept to cause mass-analyzed ions having a range of mass-to-charge ratio (m/z) values to reach the ion detector at different times. Completion of a mass scan typically requires less than a second, and covers a wide range of m/z values, typically from 50 Atomic Mass Units (AMU) per charge to about 2000 AMU per charge.

In Time-of-Flight (TOF) MS instruments a collection of ions of different m/z are simultaneously directed to an ion detector. Ions having a smaller m/z value reach the detector before those having a larger m/z value.

A typical ion detector provides an ion intensity response that is proportional to the number of ions that strike it at any given time. Thus, raw intensity data obtained from the detector is proportional to m/z values rather than to the mass of the associated ions. Often, however, the mass spectrometer's output data is simply referred to as mass data.

FIG. 2 is an example of a graph of ion intensity versus m/z, which illustrates a typical graph of data derived via MS. The spectrometer generates an array of information points having intensity values that vary with mass value, that is, with m/z value. The 2-D graph of this data is known as a scan. The peaks of a MS scan are typically sharper and more abundant than those observed in a LC chromatogram.

Though LC and MS are often used independently, some instruments combine these techniques such that the eluent of an LC column is utilized as a sample source for a MS. This compound technique, known as LC/MS, exploits both the compound separation capabilities of LC and the detection sensitivity of MS.

In LC/MS, MS produces a mass scan per unit of retention time of the LC device. The LC/MS instrument thus produces ion-intensity values associated with corresponding ion-m/z values and with chromatographic retention-time values. Because a mass scan may contain a few thousands to almost half a million data points, or more, and a chromatogram may have a few hundred to a few thousand data points, one notes that LC/MS analyses easily generate huge amounts of data, even for a single sample. Thus, a full data set obtained from a single sample often includes millions or billions of data points each associated with chromatographic retention time, m/z, and ion intensity.

For example, a 2000 AMU scan that has ten data points per 0.05 AMU to resolve a 0.05 AMU minimum peak width provides 400,000 data points per mass scan. If one scan per second is obtained during a two-hour LC run and each data point is represented by a 32-bit floating point number, the uncompressed LC/MS data set will include over ten gigabytes of computer-related data. Evaluation of such enormous quantities of data presents a significant challenge to chemical analysts.

SUMMARY

Some embodiments of the invention relate to data-analysis methods and apparatus that provide three-dimensional (3-D) visualization of, and dynamic interaction with, an entire data set of a chemically analyzed sample. Such analytical capabilities provide insights into sample data that otherwise would be difficult to obtain with prior approaches. Some embodiments of the invention mitigate the problem of manipulating large data sets by generating a display image from only the portion of the data that is most relevant to a current view.

Some embodiments of the invention arise, in part, from the realization that complex LC/MS-related data is advantageously evaluated through use of such dynamically-interactive 3-D visualizations of the data, and that full data sets are storable, by exploiting the spiky nature of LC/MS data, in a compressed manner that preserves all data.

Some embodiments of the invention provide several advantages over some previous approaches to the presentation of LC/MS data. For example, some embodiments allows analysts to both readily survey a large full set of data and then shift focus to review a portion of the set of data in greater detail. Such capabilities ease identification of, for example, peak clusters having levels near a noise level, ease confirmation of the presence of a peak, and/or provide interactive exploration of a full set of data.

Accordingly, in one aspect, the invention features a method for analyzing a chemical sample. The method includes compressing chemical-analysis data points substantially with no loss of information, storing the compressed data points in a main memory, generating, from the stored data points, nested data arrays, storing the nested data arrays in a video memory, rendering an image from the nested data arrays, and displaying the rendered image. The data points are optionally the raw data obtained from a chemical analysis of a sample.

Each data point is associated in one-to-one correspondence with a value pair of a retention-time and a m/z ratio and has an ion-intensity value. The data points are compressed by eliminating at least some of the data points that have a zero ion-intensity value. At least one of the nested data arrays has a reduced density of data in correspondence to a distance between the array and a visualization viewpoint. Moreover, each array has a linearly graded time axis and a non-linearly graded mass axis.

In another aspect, the invention features an analytical instrument for analyzing a chemical sample. The instrument includes a chromatography module, a mass-spectrometry module that receives an eluent from the chromatography module, a computer unit that receives data points from the chromatography and mass-spectrometry modules, and a monitor for displaying rendered images. The computer unit includes a processor, a video memory, and a main memory for storing instructions that, when executed by the at least one processor, implement steps such as those associated with the method described above.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 4A is a typical terrain sampling grid;

FIG. 4B is an LC/MS data-sampling grid, according to one embodiment of the invention;

FIG. 5 is a 3-D diagram of a view-point location and an associated view frustum, according to one embodiment of the invention;

FIG. 6 is a diagram that illustrates the organization of data collected as a sequence of mass scans in time ascending order, according to one embodiment of the invention;

FIG. 7 is a diagram that shows a mass-intensity association for the raw data of a single mass scan, such as one of the scans of FIG. 6;

FIG. 8 is a diagram of a single mass scan, such as one of the scans of FIG. 6;

FIG. 17 is a diagram illustrating a rendering pattern, according to one embodiment of the invention;

FIG. 18A is a diagram illustrating the drawing of a strip pattern in correspondence with an array of indices, according to one embodiment of the invention;

FIG. 18B is a diagram illustrating the drawing of an updated strip pattern in correspondence with an updated array of indices, according to one embodiment of the invention;

DESCRIPTION

Some embodiments of the invention described below relate to 3-D visualization of large LC/MS datasets. Some of these embodiments provide interactive 3-D visualization of full data sets to support data analysis. Although the description provided here focuses on the analysis and presentation of LC/MS data, one having ordinary skill will understand that more general embodiments encompass display of other genres of data, such as gas chromatography-related data and, more generally, many other genres of chemical-analysis and other data.

As described in more detail below, some embodiments employ nested hierarchical grids of data, which are optionally stored in fast video memory, to support high frame-rate 3-D visualizations of LC/MS data. Grids having a greater distance from a point of view of the display have a portion of their associated data eliminated.

In contrast to some other display techniques, some embodiments for displaying LC/MS-related data support two axes that are non-linear and/or have different numbers of data points over a full collection of data (mass points per time points of, for example, 20.) Some embodiments also exploit features of LC/MS data, for example, data spikiness, so that grids are easily merged and compressed by not storing the large number of zero-intensity points that are typical of LC/MS data. Moreover, a data density mismatch at grid-level boundaries requires no accommodation in many situations due to the spiky nature of a 3-D image of LC/MS data, according to one embodiment of the invention.

First, for context, considerations related to 2-D graphical displays of LC/MS data are described.

Figure 1:
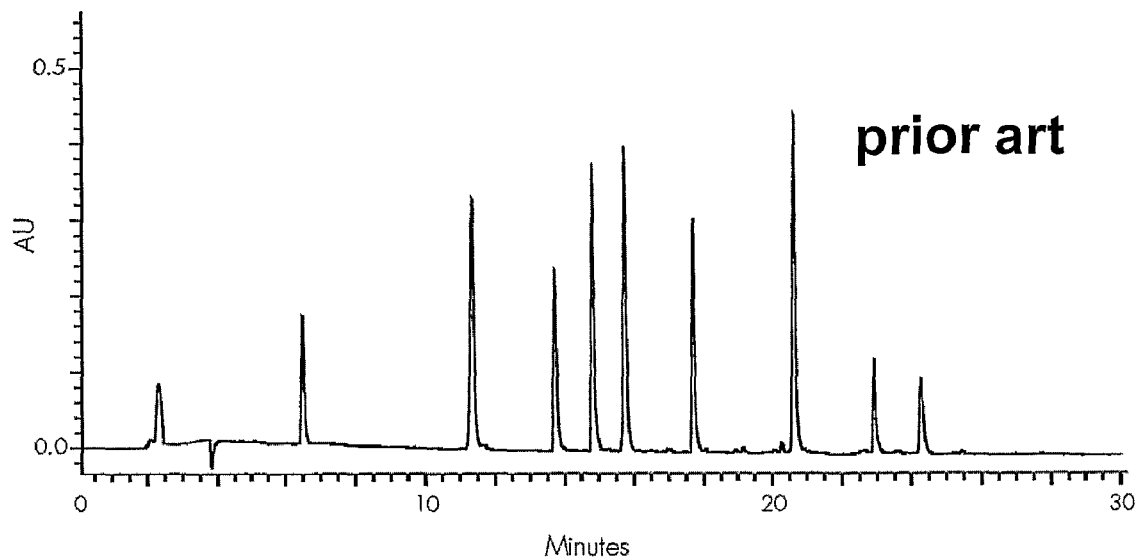
FIG. 1 is a typical LC chromatogram obtained through use of a UV absorption detector.
Figure 2:
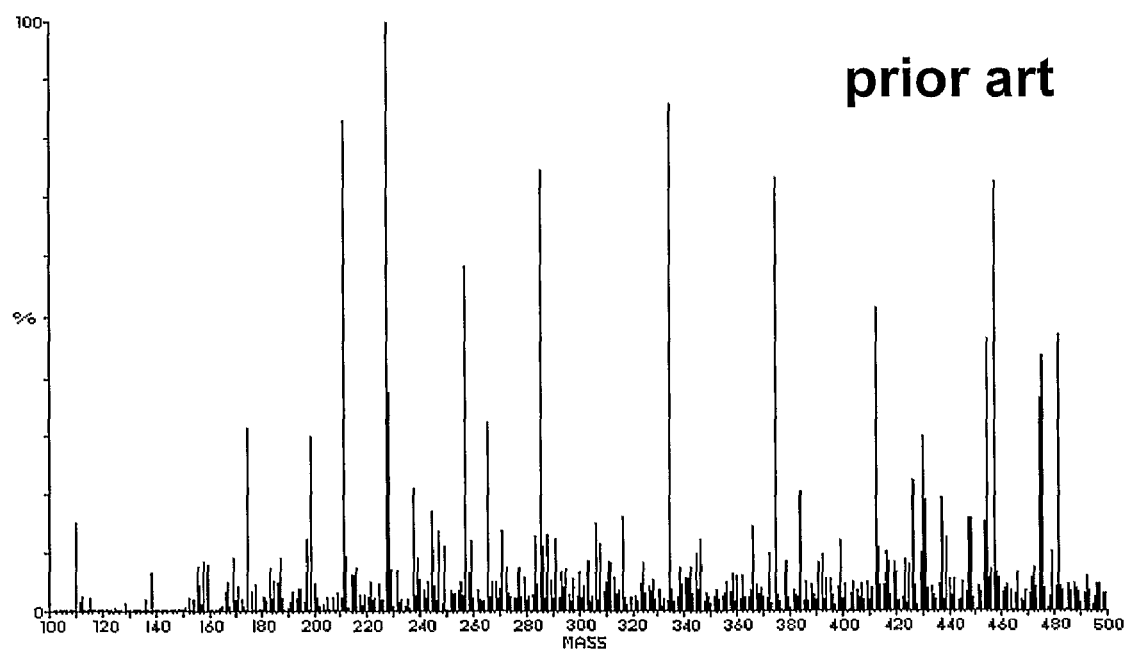
FIG. 2 is a graph of ion intensity versus m/z.

Referring again to FIGS. 1 and 2, analysts often utilize 2-D displays of LC/MS data. Since most LC/MS data sets include areas of no interest, such as portions of data having no significant intensity, an analyst having some knowledge of the data set can direct her attention to MS scans at specific retention times of interest. For example, either only the data of those areas is processed, or only the data in those areas is acquired.

If an analyst wishes to preserve all data, the analyst optionally utilizes a data averaging method that allows reduction of the quantity of stored data without compromising the information of interest. The analyst can reduce the quantity of stored data after acquisition, or the instrument can perform data reduction during acquisition. For example, the analyst optionally uses centroided data, in which only the peak apexes are analyzed.

Typically, several of these 2-D subsets are frequently required to adequately evaluate a sample. Such evaluations are often tedious. Moreover, because an LC/MS analyst typically does not collect or review all available data, she may miss important sample features.

The following description relates to embodiments of apparatus and/or methods that provide, in part, 3-D visualization of LC/MS data sets.

Figure 3:
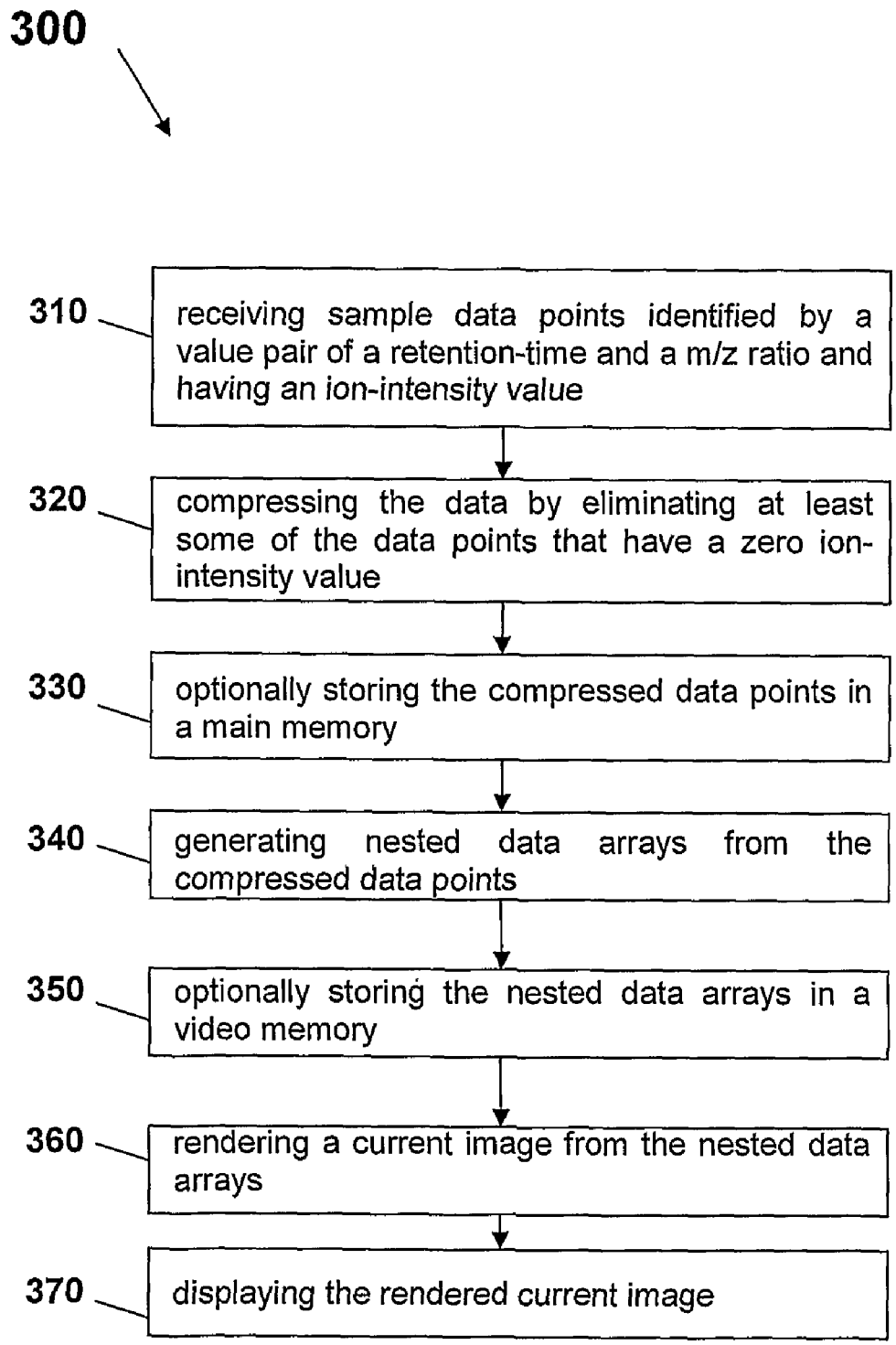
FIG. 3 is a flow diagram of a method for visualization of chemical-analysis data, according to one embodiment of the invention.

FIG. 3 is a flow diagram of a method 300 for visualization of chemical-analysis data points obtained from a sample, according to one embodiment of the invention.

The method 300 includes receiving (310), compressing (320), and storing (330) the data without loss of information. The method 300 also includes generating (340), from the stored data points, nested data arrays, storing (350) the nested data arrays in a video memory, rendering (360) an image from the nested data arrays, and displaying (370) the rendered image.

Each received (310) data point is associated in one-to-one correspondence with a value pair of a retention-time and a m/z ratio and has an ion-intensity value. Thus, a data point includes three pieces of data: a retention-time value, a m/z value, and an ion-intensity value associated with the retention-time and m/z values. A full set of data defines a 3-D surface; for the purposes of this description, m/z and retention-time values are associated with x and z axes, and intensity is associated with the y axis of an orthogonal coordinate system.

The data, such as raw data, is compressed (320) by eliminating at least some of the data points that have a zero ion-intensity value. Thus, no information is lost while the quantity of stored data is reduced from that of the full raw data set. The compressed data is optionally stored (330) in a main memory, such as solid-state memory, in a magnetic-medium disk drive, or in an optical drive, or any other suitable storage device.

As described in more detail below, at least one of the nested data arrays has a reduced density of data in correspondence to a distance between the visualization viewpoint and the x-z plane. Moreover, each array has a linearly graded time axis and a non-linearly graded mass axis.

As described below, a level-of-detail (LOD) approach is optionally used to generate (340) the arrays using only a relevant portion of detail of the stored (330) full set of data. As an analyst-selected viewpoint moves, data stored (350) in the arrays are updated from the stored (330) full set of data.

In some embodiments of the invention, the arrays take the form of nested regular grids to exploit characteristics of LC/MS data. Such data, although not completely regular, is conveniently organized in rows and columns.

The nested rectilinear grids support the LOD viewing of the full data set. That is, as a particular portion of visualized data is approached, the visualization reveals greater detail through greater resolution of the corresponding data, i.e., more of the data associated with that image portion. Each grid level, or LOD, holds a portion of the full data at a particular reduced resolution associated with distance from a viewpoint. The levels of data are stored in video memory using, for example, toroidal addressing, as described in more detail below.

In each grid level, only a moving section of the data is displayed in the screen, and in that section, the area occupied by the next level is excluded. As the view point moves, the LOD levels are sequentially updated with new data transferred from the full set of data. Grids are described in more detail below with reference to FIG. 4B.

Each rectangle grid represents a section of the data at different levels of resolution. For example, a nearest rectangle optionally retains all associated data, while more distant rectangles have a portion of their associated data eliminated, as a function of distance. Optionally, for example, each level steps down in detail by a power of two.

Although the following description refers to nested regular grids, one of ordinary skill will recognize that described principles are applicable to data arrays having a variety of forms. Some preferred embodiments use regular grids of rows and columns rather than an irregular grid. Although LC/MS data is not evenly spaced in either the time or mass axes, it is regular in the sense that it may be organized as rows and columns of data points. The data is typically collected as a series of mass scans, collected for different retention times. Each scan may be associated with a row (or column) of data. Some alternative embodiments utilize irregular grids.

Although LC/MS data is optionally treated as having some similarities with topographical data, there are also substantial differences. Typically, terrain-related elevation data describes a relatively smooth surface having few or no abrupt characteristics like the peaks that are characteristic of LC/MS data. Moreover, the spike-like features of some LC/MS data are often separated by relatively flat sections of data.

Terrain topography is conveniently sampled at regularly spaced intervals in two horizontal length axes. Grids are desirably arranged in a centered pyramid-like layering to support the ability to rotate a viewpoint situated over the terrain to look in different directions.

In contrast, LC/MS data usually has non-regular sampling intervals, which are different in the two horizontal coordinates of some embodiments of the invention. Moreover, m/z sampling is usually non-linear with approximately ten times or greater sampling than the sampling associated with a time axis. Thus, tessellation of LC/MS data is often relatively difficult, possibly causing unexpected results.

Moreover, a full data set is optionally displayed (370) with a viewpoint residing entirely to one side of the data set. That is, the viewpoint optionally does not reside over the data set, i.e., over any retention time-m/z value pair of data in the set. For example, a pivot point associated with the viewpoint does not lay over the data.

To support such a view, in some embodiments nested grids are generated (340) such that the grids are not centered with respect to one another. For example, all grids optionally share a border along the edge of the data set closest to the viewpoint.

FIG. 4A shows an example of a typical terrain sampling grid 400A, and FIG. 4B shows an example of an LC/MS data-sampling grid 400B, according to one embodiment of the invention. The mass-axis sampling is non-linear and broken occasionally with bursts of samples. The time-sampling rate is optionally regular; in some cases, regularly spaced retention-time values are missing because, for example, an instrument interleaves a scan for other purposes. The points of the grid are associated with intensity values obtained via mass spectrometry and associated with the corresponding values of retention time and m/z.

Next referring to FIG. 5, some embodiments provide 3-D visualization of all or a portion of a data set in response to analyst selections. FIG. 5 is a 3-D diagram of a view-point location and an associated view frustum. The diagram illustrates how a portion of a set of nested arrays used for rendering (360) is selected. The selection is made in response to analyst selections of time, mass, and/or intensity scales and/or position relative to the data set. The diagram illustrates a viewpoint 540, field-of-view angles 550, and a view frustum 510, which is bounded by a near plane 520 and a far plane 530.

The view point 540, also referred to herein as the camera eye position, is the selected location of the observer (the camera) with respect to the 3-D data set. The view frustum 510 is the volume enclosed by the truncated projection pyramid determined by the field-of-view angles 550 and the near and far planes 520, 530. Only data located inside the view frustum volume are displayed via a display screen.

The grids only include data that are required for the current view. If the view point 540 is far away from the data, the details are not shown. As the view point 540 approaches the data, the detail that is visible increases, but the field of view decreases. At an appropriate distance, the full detail appears.

This balance between visible detail and field-of-view ensures that the amount of data relevant for a particular view is approximately constant, and this data requires less memory than the full data set. Some embodiments utilize fast video memory to store grids' data while main memory stores the full data set. This approach provides efficient utilization of the different types of memory typically present in conventional or specialized computer systems.

In various implementations, an analyst manipulates the selected viewing conditions to support study of a set of data. For example, the analyst rotates the view point 540 relative to the data to observe the data from any angle, both in azimuth or elevation, and moves closer to or farther from the data.

As will be understood by one having ordinary skill, various implementations provide monochrome shading, color shading, and/or lighting effects. For example, an analyst optionally moves the location of a light source. Some implementations, for example, utilize a color pattern that gives the analyst an indication of the relative intensity of each peak. Optionally, the analyst selects a monitor-displayed peak, and, in response to the selection, the time, mass, and intensity values for the peak are shown on the screen.

Some preferred implementations of the invention utilize object-oriented programming known to one having ordinary skill in the programming arts. For example, various features of the method 300 are optionally implemented as functions within the C++ programming language.

One example of features that are optionally implemented in the method 300 via programming techniques are described next. The retention-time values associated with LC/MS data are placed in a 1-D texture, the mass values in another 1-D texture, and the intensity values in a 2-D texture. With this arrangement, to render (360) a geometry point, only two texture coordinates are required to retrieve required data: one for the time and one for the mass.

The time coordinate is used to fetch a time value from the time 1-D texture, the mass coordinate is used to fetch a mass value from the 1-D mass texture, and both texture coordinates are used to fetch the corresponding intensity value from the intensity 2-D texture. A similar process is optionally used to obtain other properties of each data point, such as a normal vector or color, if corresponding 2-D textures included.

As mentioned above, an illustrative embodiment uses a LOD approach in generating (340) nested regular grid rectangles and rendering (360) images for display. As described in more detail below, different grid levels are synchronized, while only a moving section of the memory being displayed is updated. Memory updates occur as the view point moves and without drawing an overlap of adjacent levels. In some illustrative embodiments, the junctions between grid levels do not create substantial artifacts and thus require no accommodation for rendering (360) to avoid image artifacts.

In the present example, the time and mass resolution are assigned to each grid level as follows. Given that the resolution in the mass axis is higher than in the time axis, there are more LOD levels in the mass axis than in the time axis. Therefore, some grid levels have the same time resolution. Alternatively, one commences generating (340) nested regular grid rectangles at the coarsest LOD level, assigning the coarsest resolution to both the mass and the time. Then, grid levels with increasing resolution utilize increasing resolution in mass and in time, until a grid level reaches the finest resolution level in time. Subsequent grid levels having increasing resolution maintain the time resolution at the finest level, and increase the mass resolution only. This resolution assignment to grid levels may create unexpected results at the boundaries of levels with the same time level but substantially different mass levels.

Alternatively, as described in more detail below with reference to FIG. 10, the level assignment starts from the finest level rather than from the coarsest level. The finest resolution grid has both the mass and the time at the finest resolution. Decreasing resolution grid levels have decreasing resolution in both mass and time, until some grid level reaches the coarsest resolution in time. Subsequent grid levels of decreasing resolution maintain the time resolution at the coarsest level and decrease the mass resolution only. In this case, the boundaries of levels with the same time level but different mass level occur at the coarser resolutions, and the transitions between higher resolution levels are relatively smooth.

An alternative assignment of orthogonal axes to LC/MS data axes associates time with the x axis, mass with the z axis, and intensity with the y axis. Alternately, the axes assignment are changed to mass in the x axis, time in the z axis, and intensity in the y axis. This optionally lead to the data organization in rows parallel to the x axis, which supports storing of the data in arrays. Some embodiments support axis swapping during the rendering (360).

As described above, data is preferably compressed (320) to store (330) data structures in main memory in a lossless compressed form. The data structures are optionally hidden from other software components so no knowledge of the compression is required by the other components.

During some cases of data collection, an LC/MS instrument interleaves mass scans obtained with different instrument conditions, and stores all scans acquired with particular instrument conditions into a function data file. Other functions data files would contain scans acquired with different instrument conditions. For example, the instrument could use one of every ten scans to calibrate itself, and store all calibration scans in a separate function data file, instead of storing them in the same data file where the normal acquisition scans are stored.

Interleaved scans are one cause of an irregular sampling rate of the data in the time axis. The different functions contained in a data directory are optionally distinguished by a function number assigned by the analyst at the time of the analysis according to some convention of her choice.

FIG. 6 is a diagram that illustrates the organization of data collected as a sequence of mass scans in time ascending order. The data organization includes a series of mass scans 610, collected in time one after another.

FIG. 7 is a diagram that shows a mass-intensity association for the raw data of a single mass scan collected at time t, such as one of the scans 610 of FIG. 6. The single scan 700 is associated with its time of acquisition, and includes a sequence of mass value 710 and intensity value values 720 in pairs. In the diagram, "p" is the number of pairs in the scan. The pairs are sorted in ascending order of mass value.

FIG. 8 is a diagram of a single mass scan 800, such as one of the scans of FIG. 6. A typical mass scan includes many mass values that have zero associated intensity. This feature of mass chromatograms is exploited to save raw data to a file All mass-intensity pairs with zero intensity value are discarded prior to saving, except for those that are adjacent to a non-zero intensity pair (810) as illustrated in FIG. 8. The figure shows a diagram of a single mass scan 800, as obtained from the raw data, such as one of the scans 610 of FIG. 6.

This example of lossless compression reduces the size of saved data, but still has some redundancy as the remaining zero-intensity pairs are generally not required to preserve a full sample data set. As described with reference to FIG. 9A and FIG. 9B, a preferred compression (320) approach eliminates this redundancy and replaces the mass-intensity pairs with pairs formed of a mass index and an intensity value. Further reduction in stored data provides a reduction relative to collect raw data of, for example, approximately 35%. Accordingly, in the present example, each intensity value is addressed with a pair of indices, a time index and a mass index.

Figure 9A:
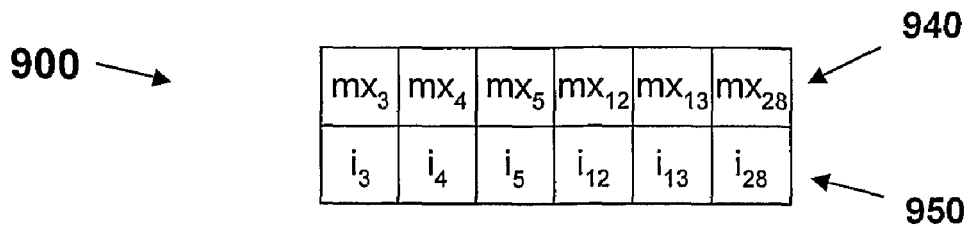
FIG. 9A is a diagram of a scan object corresponding to the mass scan of FIG. 8.
Figure 9B:
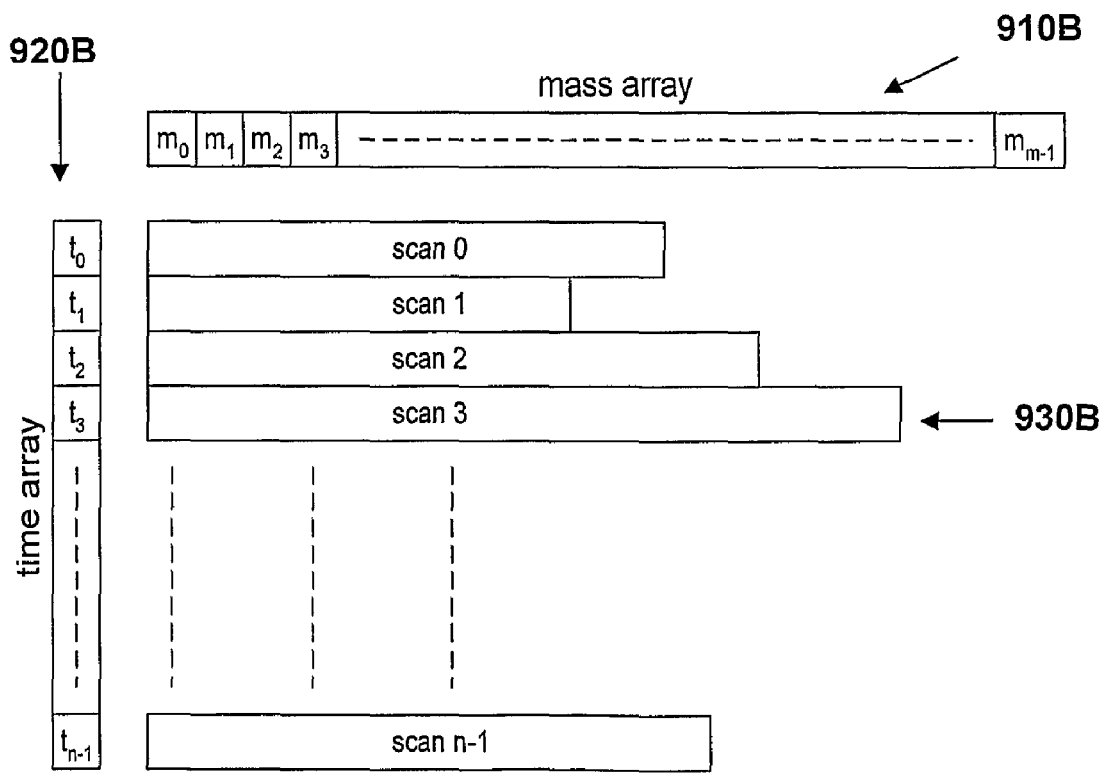
FIG. 9B is a diagram that shows a compressed data structure, according to one embodiment of the invention.

FIG. 9A is a diagram of a scan object 900, including mass indices 940 and an intensity values 950, which corresponds to the mass scan of FIG. 8, where $mx_i$ is the $i^{th}$ mass index. FIG. 9B is a diagram that shows a compressed data structure that includes a mass array 910B, a time array 920B, and an associated array of scan objects 930B such as the scan object 900. There is one object 930B for each mass scan in the data, each scan associated with a corresponding retention time.

All the mass values are placed in an array 910B that is addressed with a mass index. Similarly, all the time values are placed in another array 920B that is addressed with a time index. Both arrays are sorted in ascending order. All the non-zero intensity values are placed in a data structure 930B addressable with the mass and time indices.

The data organization of this example hides all the data storage details from client functions, as may be implemented, for example, utilizing C++ coding techniques known to one having ordinary skill. The clients then only must pass a pair of indices to receive in return an intensity value, even if the intensity value was a non-stored zero value. That is, if the indices address a non-stored value, a zero value is returned. The clients need not be aware of this internal behavior.

The time values array 920B is optionally built in the following manner. The scan times are placed in the array in ascending order. The mass values array 910B is optionally built in the following manner.

Given that, as described earlier, each mass scan has only the mass values that have a non-zero intensity value associated with them and a few more mass values with zero intensity associated, each scan does not have all possible mass values present in the data. Therefore, in order to find all the mass values present in the data, each scan is read and the mass values array is filled with only the mass values that are not already in the array. Once all mass scans have been read, the mass array contains all possible mass values present in the data. To sort them in ascending order, the values are sorted as they are being read, instead of after completion of reading. Such an approach optionally speeds the observation of new mass values while the scans are tested.

In some implementations, the intensities data structure (930B) is built after the mass values array is completed. In this case, the mass scans are read twice, one to build the mass values array, and a second time to build the intensities data structure.

A scan object maps a key to a value, with the key being the mass index described above, and the value an intensity value.

An array stores the keys, i.e., the indices, and another array stores the values, both sorted in ascending order and having the same size. To fill the arrays, for each non-zero intensity value read, a new key-value pair is added. The pair includes the intensity value as the value, and the index corresponding to the mass value as the key.

Data reduction in the compressed (320) data is optionally done in the mass axis only, and optionally entails sampling the mass at regular intervals to obtain the mass axis points. In some implementations, an analyst defines the mass sampling interval and, for each scan, the intensity at each mass point is calculated by adding all intensities corresponding to masses that fall within each interval. The reduced data is optionally stored using the same compression technique as described above for the raw data.

Next referring to FIG. 10 through FIG. 16, grid level formation and features of generating (340) nested arrays are described in more detail for some illustrative examples.

The full data set stored (330) in main memory provides the source of data for generating (340) grid-related data to be stored (350) in video memory. The grid-related data has different levels of resolution depending on the LOD level of the grid, and this reduction is optionally different in time and in mass.

For example, during generating (340) nested arrays, a mass level and a time level for data reduction are included with a request for stored (330) data. In response, reduction is performed on the returned data. A data reduction criterion is optionally a maximum intensity value. That is, the intensity of the data point returned is the maximum intensity found in the number of data points considered in the reduction.

Data reduction for grid generation (340) is optionally done in the mass axis only, and optionally entails sampling the mass at regular intervals to obtain the mass axis points. In some implementations, an analyst defines the mass sampling interval and, for each scan, the intensity at each mass point is calculated by adding all intensities corresponding to masses that fall within each interval. The reduced data is optionally stored using the same compression technique as described above for the raw data.

Grid levels are optionally identified by a number that ranges from zero for the level with the finest resolution to some positive number for the level with the coarsest resolution. The zero level is referred to herein as the lowest level though it is associated with the highest data resolution.

During generation (340) of grid levels, when a new data file is read, a number of levels is optionally selected in response to an amount of data to be used. For example, the number of data points in the mass direction and in the time direction are examined; as the number of data points in each direction is generally different, an independent tessellation value is defined along with highest levels for the mass axis and for the time axis.

The following discussion applies independently to the mass and time axes; references to the number of points indicate the number of points in one of the axes, not the total number of points in a grid level, which generally is obtained by multiplying the number of points in both axes.

Given the disparate resolution of the time and mass axes (about a hundred times higher mass resolution), there are almost always more levels for the mass axis than for the time axis, which means that there are grids having different mass sampling density but having the same time sampling density. The number of grids to use is determined by the highest level number found (normally the highest mass level).

Figure 10:
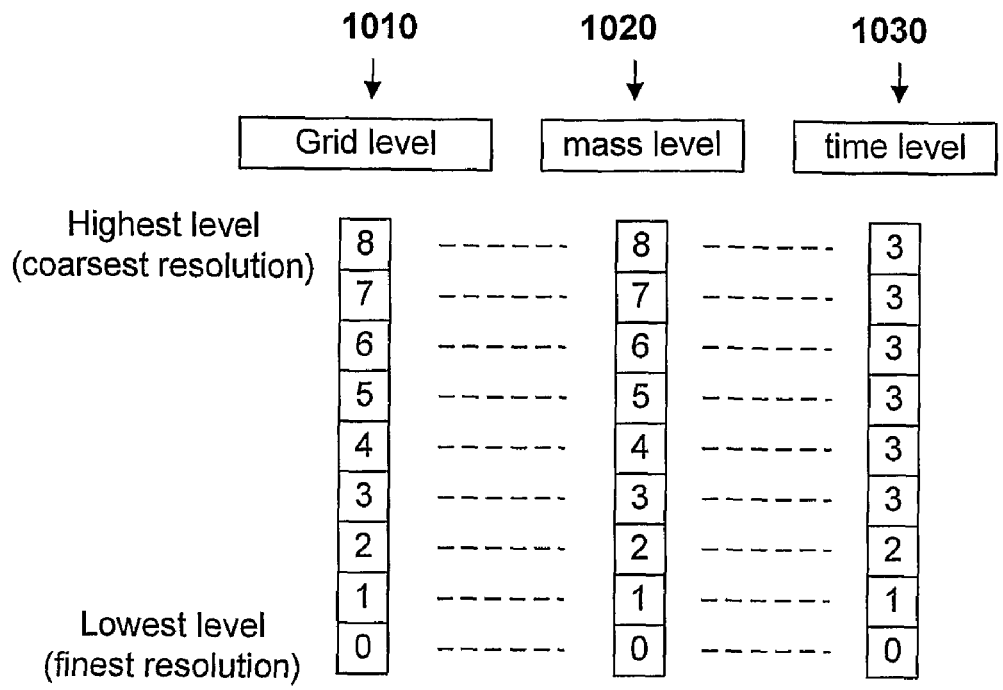
FIG. 10 is a diagram of nine grid levels, according to one embodiment of the invention.

Referring to FIG. 10, a criterion optionally used to assign mass and time levels to each grid is as follows. A grid of level zero has both mass and time at level zero. Higher grid levels have both the mass and the time levels increasing by one level. Once a grid reaches the highest level in mass or in time, subsequent higher grid levels maintain that highest level reached.

FIG. 10 is a diagram illustrating an example the association of nine grid levels 1010 with mass levels 1020 and time levels 1030. The grid levels 1010 have a highest mass level of eight (nine mass levels) and a highest time level of three (four different time levels.) Levels 0 through 3 have mass and time levels 0 through 3. Grid levels 4 through 8 have mass level 4 through 8, respectively, but they all have a time level of 3, the highest time level.

As a result of the different tessellation and data-point spacing between the mass axis and the time axis, the data areas covered by the grids are generally far from being squares. They are optionally thought of as thin rectangles oriented parallel to the time axis, although an analyst may reshape the rectangles by selection of scaling.

Figure 11:
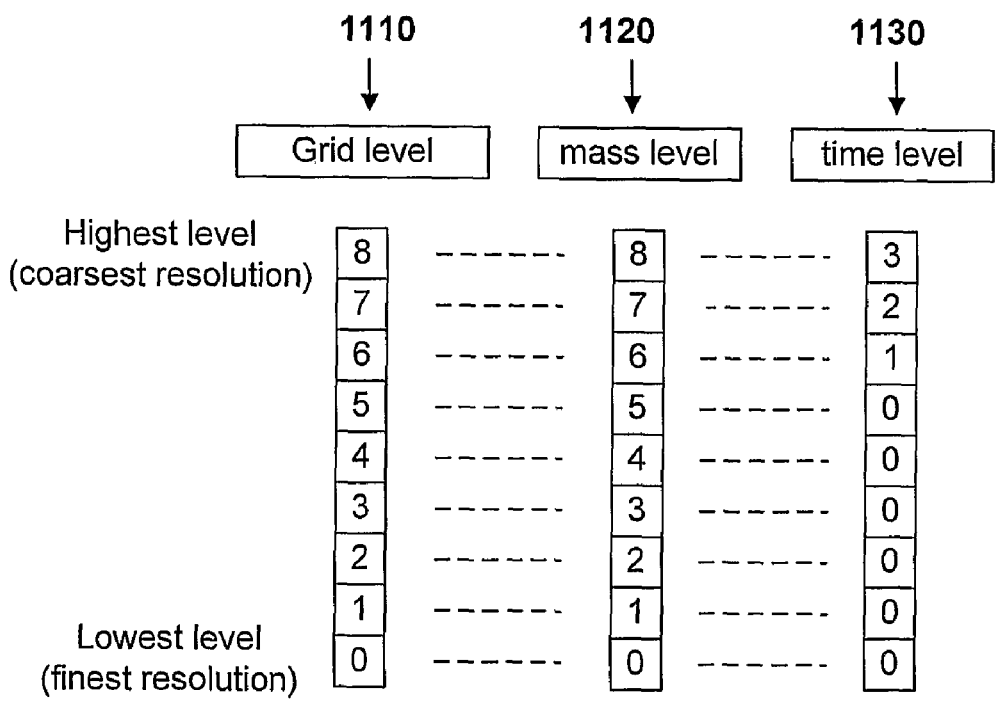
FIG. 11 is a diagram of nine grid levels, according to one embodiment of the invention.

An alternate distribution of mass and time levels is illustrated in FIG. 11, which is a diagram illustrating an example of nine grid levels 1110 with mass levels 1120 and time levels 1130.

This example is similar to the levels 1010, 1020, 1030 of FIG. 10, but the time level distribution is different. In these levels 1110, 1120, 1130, the highest time level is assigned to the highest level grid and the time level is decreased for lower level grids until a time-level zero is reached.

Subsequent lower level grids maintain a time level at zero. This time-level distribution provides a maximum time resolution in as many of the grids as possible, given the large resolution difference between the mass and the time axes. This example, however, in some cases the mass resolution difference is quite noticeable in a display image when depicting a transition between the sixth grid and one of the low-level grids.

Figure 12:
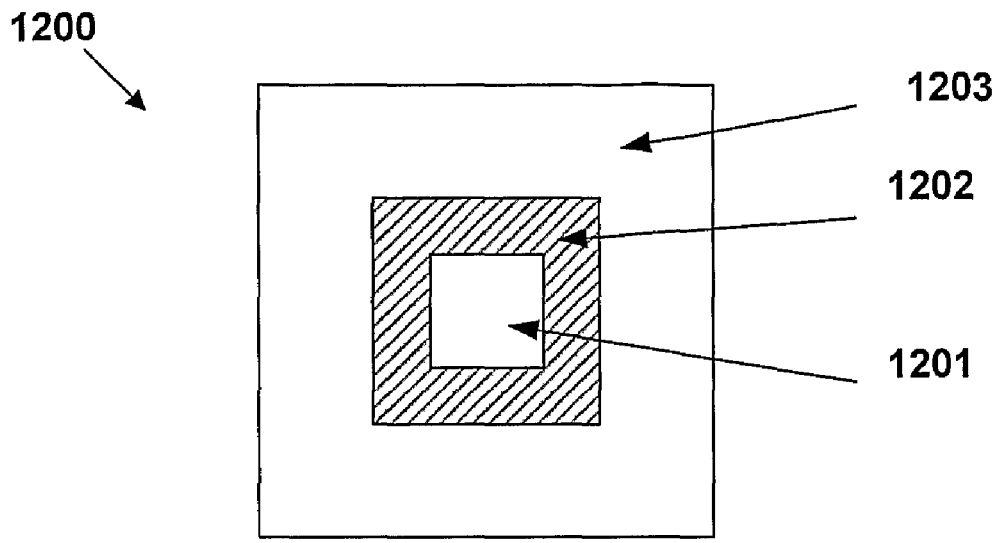
FIG. 12 is a diagram of a grid level, according to one embodiment of the invention.

Next referring to FIG. 12 through FIG. 16, examples of memory updates of grid levels in support of generating (340) data arrays are described. FIG. 12 is a diagram of a grid level 1200. In this example, the grid level has three regions of data, referred to herein as a memory area 1203, a draw area 1202, and a hole area 1201. As mentioned earlier, grid's data is optionally stored in a video memory (350).

The draw area 1202 identifies the portion of the grid's data that is shown in a display, the hole area 1201 identifies a region occupied by the next lower level grid, and the memory area 1203 identifies the region that is stored (350) in video memory (the entire grid's data).

In this example, the memory area 1203 is selected to be twice the dimension of the draw area 1202 in each direction, supporting drawing without delay if the draw area 1202 moves within the memory area 1203. The hole area 1201, in this example, is half the size of the draw area in each direction, because the size of adjacent grids levels, in this example, varies by two.

Figure 13:
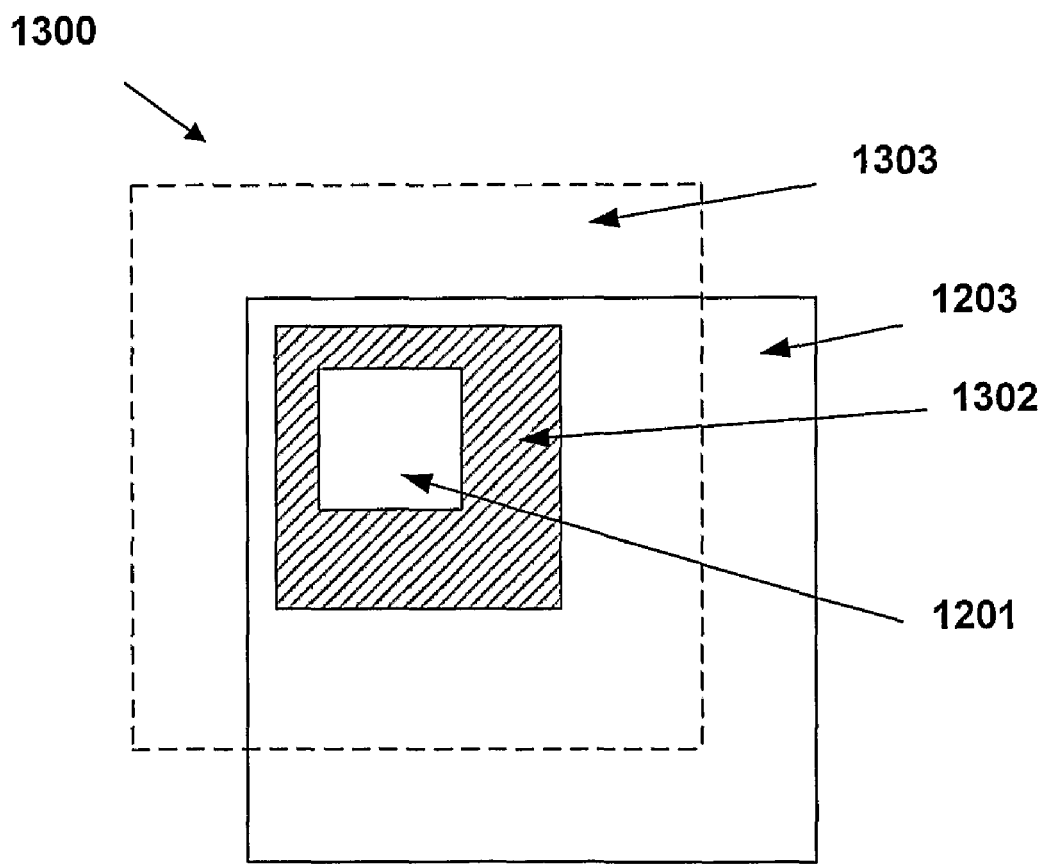
FIG. 13 is a diagram illustrating a response, to view movement, of memory areas illustrated in FIG. 12.

FIG. 13 is a diagram that illustrates the response of memory areas illustrated in FIG. 12 to view movement. The diagram includes a current memory area 1203, a new memory area 1303, a new draw area 1302, and a hole area 1201.

A position of the nested grids within the entire data set is determined by the position of the view frustum, as described above with reference to FIG. 5. As the view frustum moves the position of the nested grids with respect to the full set of stored data moves in response, if the movement is sufficiently large.

If the movement is small, the draw area 1302 moves within the current memory area 1203, and the display response is immediate. If, however, the draw area 1302 moves too close to, or beyond, the border of the current memory area 1203, the memory area is shifted to the new memory area 1303 such that the new draw area 1302 is optionally centered in the new memory area 1303.

Optionally, a proximity indicator is implemented to continuously evaluate the proximity of the draw area to the memory-area border and to trigger a memory update in response to a pre-selected proximity condition.

Figure 14:
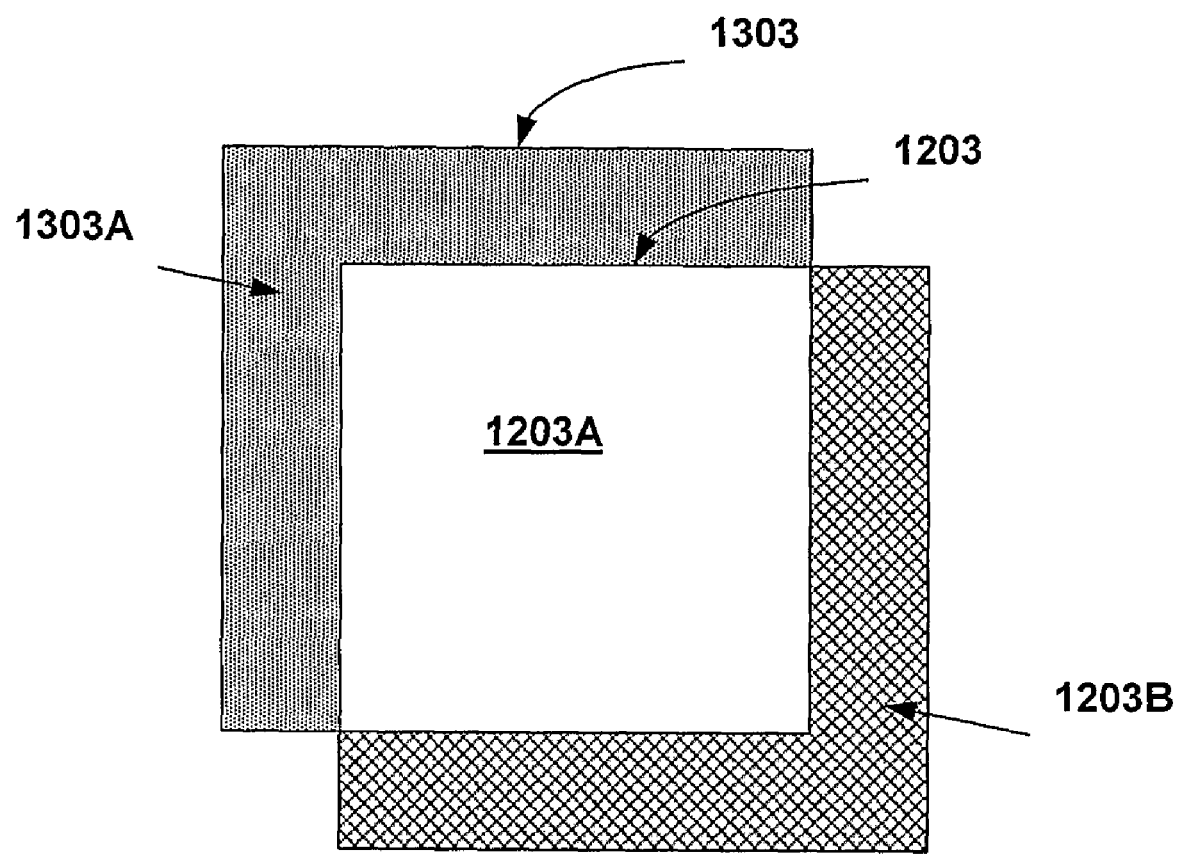
FIG. 14 is a diagram illustrating the updating of the memory of FIG. 13.

FIG. 14 is a diagram that illustrates the updating of memory illustrated in FIG. 13. To move the memory area, the new memory area 1303 is updated with new data 1303A from the compressed lossless full data set stored in main memory. The memory area 1303 need not, however, be entirely refilled; the memory area 1303 retains at least some current data 1203A and updates the new data 1303A is necessary. Thus, the new memory area 1303 includes some new data 1303A and some retained data 1203A. Moreover, the current memory area 1203 has some discarded data 1203B that is no longer needed for the new memory area 1303.

In some implementations, memory area updates are performed via toroidal addressing, which helps inserting, new data at the correct location inside the grid's data array, overwriting the old data at that location.

Toroidal addressing provides circular buffering for two-dimensional data arrays. In a circular buffer, where the data at the end of the array continues at the beginning of the array, an offset from the beginning of the array marks the start of the data sequence. Each row of the 2-D array is a circular buffer, and the sequence of rows is a circular buffer too, i.e., the row sequence after the last row continues with the first row. Therefore, two offset values from the beginning of the 2-D array determine where the data sequence starts.

A pair of toroidal offset indices are used to track where the memory area origin is located within the grid's data array. The array used to store the data is organized in rows parallel to the mass axis, in association with the data organization in mass scans. The number of points in each row is equal to the grid's mass tessellation number, and the number of rows is equal to the grid's time tessellation number. When the array is loaded for the first time, the rows are in time-sequential order, each row is in mass-sequential order, and the memory area origin coincides with the array origin.

Figure 15:
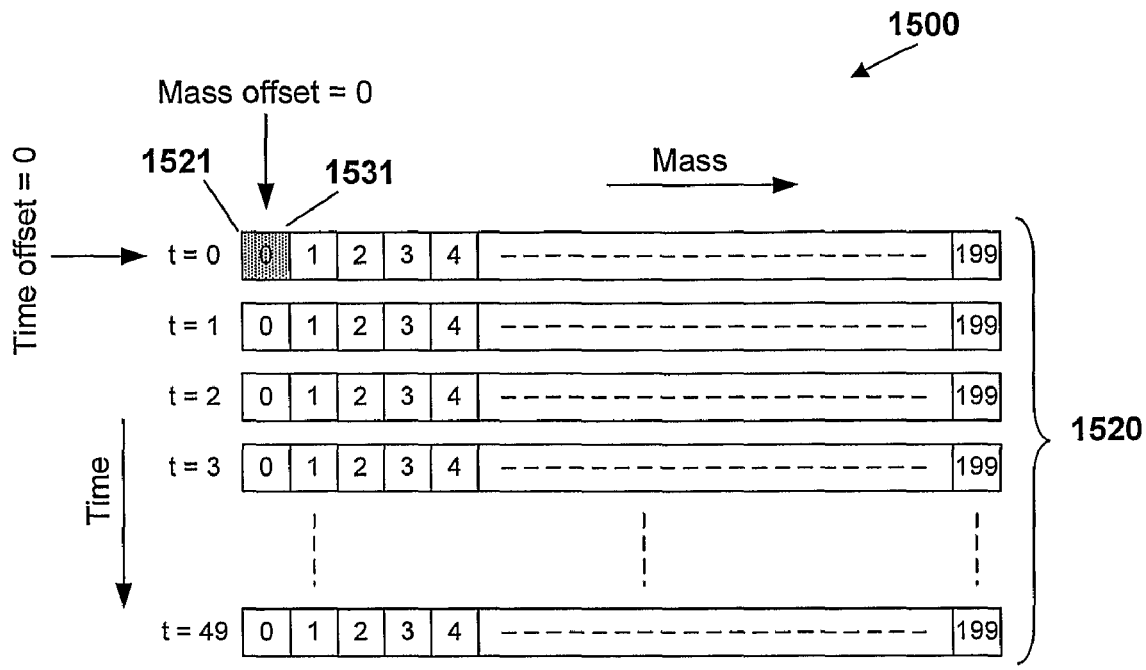
FIG. 15 is a diagram of a grid's data array that illustrates toroidal addressing, according to one embodiment of the invention.

FIG. 15 illustrates an example of a grid's data array 1500 having rows 1520 of data. The grid has a mass tessellation of 200 and a time tessellation of 50. In an initial state, the origin 1521 of the array and the origin 1531 of the memory area coincide, and mass and time toroidal offsets are zero.

Figure 16:
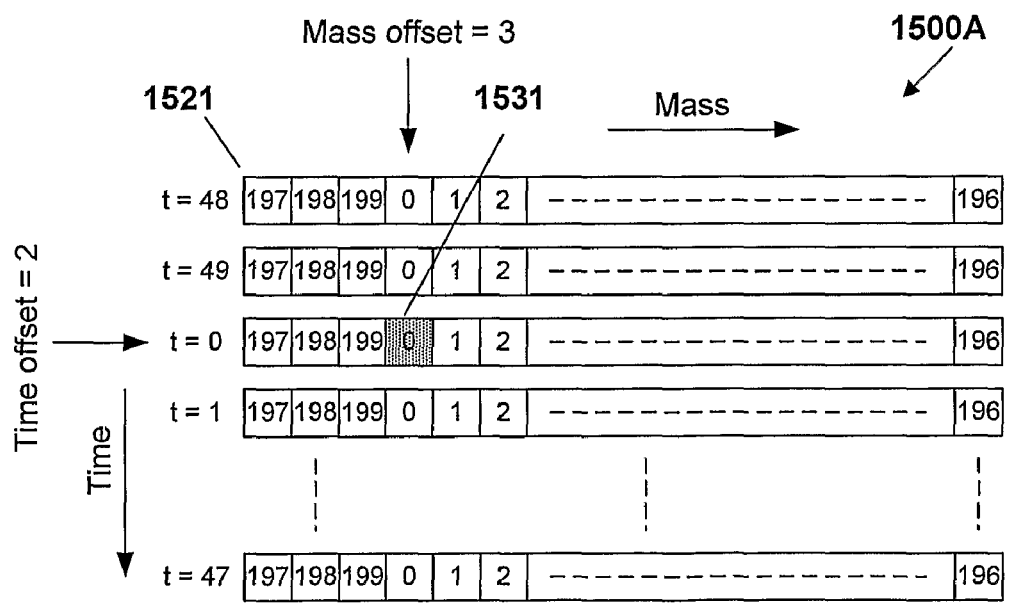
FIG. 16 is a diagram of an array that is an updated version of the array of FIG. 15.

FIG. 16 illustrates an array 1500A that is an updated version of the array 1500. The mass toroidal offset is selected to be 3 and the time toroidal offset is selected to be 2. The memory area origin 1531 and the array origin 1521 no longer coincide. These two offsets are used to properly de-reference data. Note that each row of data occupies a parcel of the array, and the mass toroidal offset is applied to the data within that parcel without invading the data in the adjacent parcels.

To support rendering (360) of the draw area, the position of the memory area, the position of the draw area, the position of the hole area, and the two toroidal offset indices are tracked. Triangle strips are used for rendering (360) the image. FIG. 17 is a diagram illustrating a triangle strip pattern 1700 for the present example. The strips run parallel to the mass axis, following the organization of the data of the arrays 1500, 1500A. Each triangle strip is defined by the points of two adjacent rows of data.

To draw the triangle strips, the data in the array is read from the stored (350) data and the toroidal addressing is dereferenced. Dereferencing the time axis determines which triangle strip inside the array is going to be drawn, and dereferencing the mass axis determines where within the rows of data the triangle strip should start.

In this example, different approaches are used to dereference the time and the mass axes. For the time axis, the toroidal offset is added to a virtual address and the modulo operand is used to get the actual address. The toroidal time offset is added to the time position of the triangle strip to draw, and the modulo operand is applied to get the actual position inside the data array.

Once the triangle strip to draw has been addressed, the mass axis is dereferenced to find the mass position to commence drawing of that strip. FIG. 18A and FIG. 8B respectively show diagrams that respectively illustrate drawn strip patterns 1810A, 1810B in correspondence with arrays of indices 1820A, 1820B. The triangle strips are drawn using the arrays of indices that address each point in the correct sequence to produce the triangles.

FIG. 18A depicts an example in which the first triangle to draw is at the beginning of the addressed rows of data, and shows the array of indices to produce the triangle strip. FIG. 18B illustrates how the array of indices are modified if the first triangle to draw is not at the beginning of the addressed rows of data due to a toroidal mass offset of 3.

Figure 19:
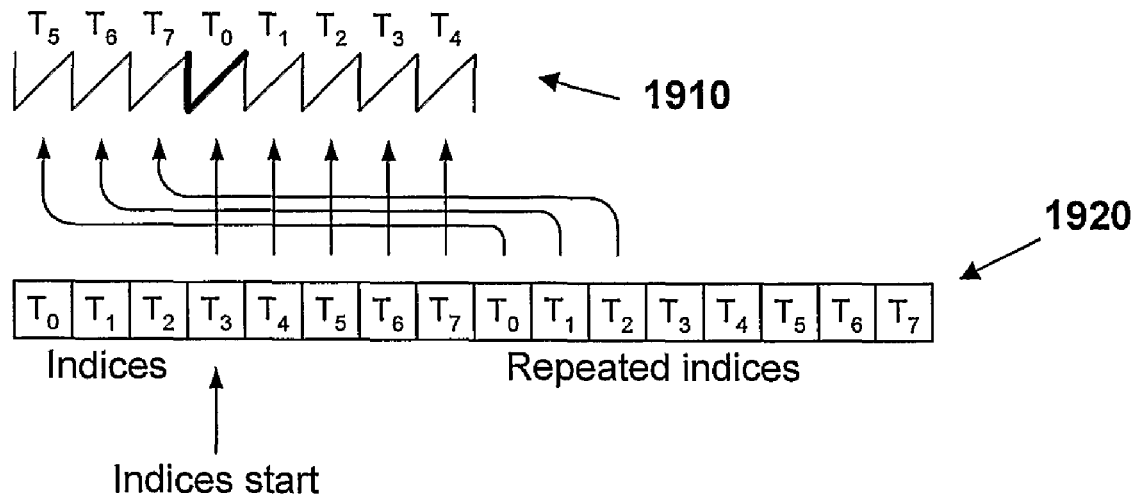
FIG. 19 is a diagram illustrating the updated strip pattern of FIG. 18B in correspondence with a doubled array of indices shown in FIG. 18A.

This technique of handling the toroidal mass dereferencing involves re-computation of the indices array every time the toroidal addressing changes. Referring next to FIG. 19, one preferred embodiment does not require re-computation of the indices.

FIG. 19 is a diagram illustrating an array of indices 1920 that is not modified from the original configuration shown in FIG. 18A. This example utilizes an array of doubled size; the second part of the array 1920 repeats the same index sequence as the first part of the array 1920. Rather than starting the indices at the beginning of the array 1920, the indices start at the location that corresponds to the toroidal mass offset. The triangles drawn from that point to the end of the rows of data (as shown in the strip pattern 1910) are produced by the indices in the first part of the array of indices, and the rest of the triangles are produced by the indices in the second part of the array of indices.

Figure 20:
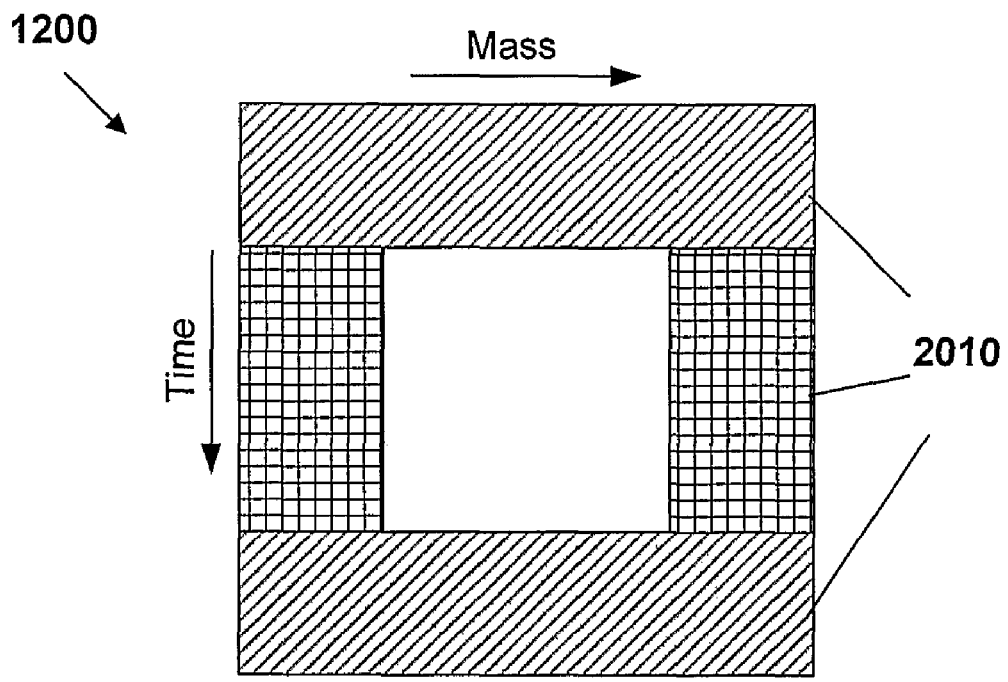
FIG. 20 is a diagram of a grid's draw area illustrating four sectors, according to one embodiment of the invention.

Next referring to FIG. 20, if a grid does not have a hole (for example, when the grid is the lowest visible,) the entire draw area is drawn using triangle strips that follow the mass axis, as described above. If the grid needs to be drawn with a hole, the draw area is partitioned, for example, into four sectors and each sector is drawn. FIG. 20 is a diagram of a draw area 2000 illustrating four sectors 2010.

In some implementations of the method 300, the change in position of the viewpoint and the view frustum determines a new location of the grids' draw area and which grids are visible.

Figure 21:
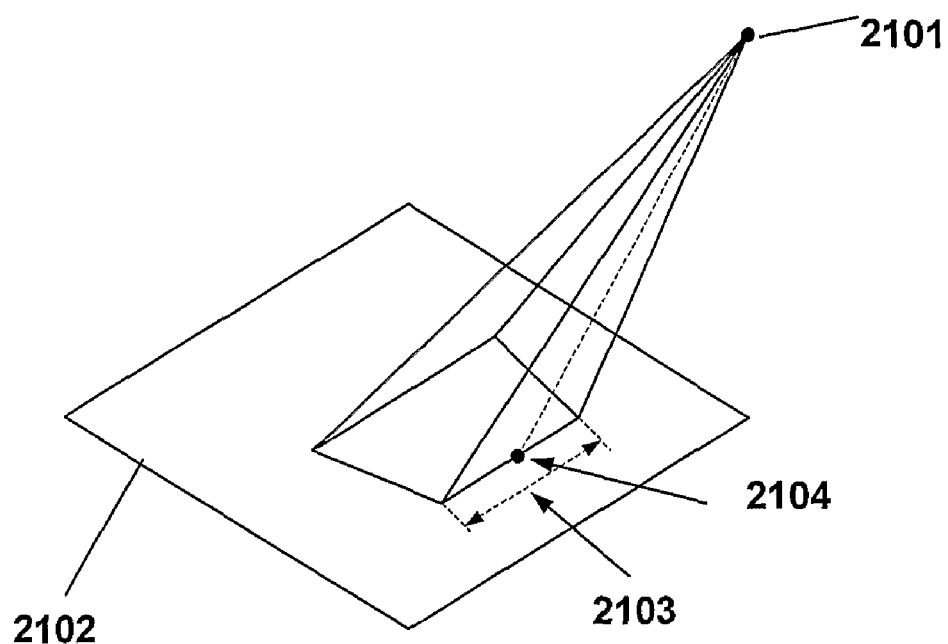
FIG. 21 is a 3-D diagram illustrating an intersection of a view frustum with a horizontal plane, according to one embodiment of the invention.

FIG. 21 is a 3-D diagram illustrating the intersection of the view frustum with the horizontal plane (the mass-time plane). The diagram shows a view position 2101, the horizontal plane 2102, the frustum intersection width 2103, and the LOD center 2104. The position of the nested grids within the entire data area is determined by the position of the view frustum such that the nested grids are centered at the point of the view frustum's intersection with the horizontal plane 2102 that has the shortest distance to the camera eye position 2101, i.e., the LOD center 2104.

The LOD center 2104 moves toward the center of the frustum when the view direction is vertical, and coincides with the center of the frustum-plane intersection when the view direction is perpendicular to the plane. The width 2103 of the frustum intersection at the LOD center point 2104 is used to determine which is the lowest (higher resolution) grid that should be drawn.

A large width indicates that the camera is relatively far or the field of view is wide. In either case, only low resolution grid levels (high levels) are allowed to draw, and high resolution levels (lower levels) are marked as invisible. In contrast, if the width is small, higher resolution levels are allowed to draw.

If as a result of a view-frustum movement some grids need to be updated, they are temporarily made invisible until each grid's update is completed. The grids are updated starting from the highest level (lower resolution) and continues with lower levels (higher resolution) in sequence. Furthermore, a draw refresh is done after each grid's update, which results in a sequence of interleaved updates and draws, with the visual effect of, for example, a progressive increase in resolution.

The view of the entire data set is scaled such that it fits inside an imaginary cube. The analyst, however, optionally sets additional scaling that modifies the form factor of the viewed data inside the cube.

Figure 22:
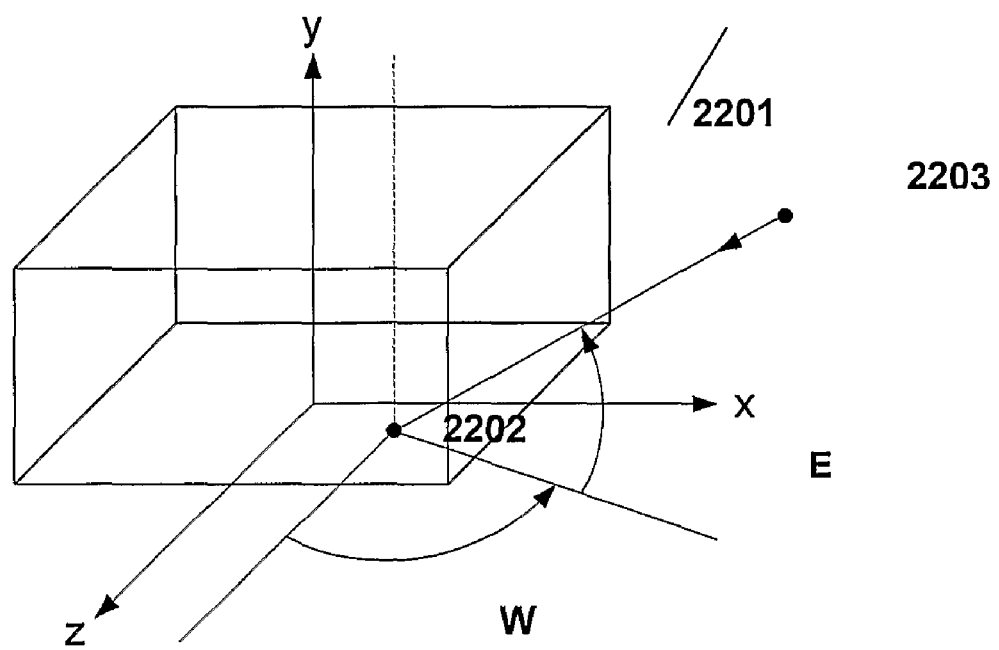
FIG. 22 is a 3-D diagram illustrating a geometrical relationship between a volume of viewed data, a "look-at" point, and a camera eye, according to one embodiment of the invention.

FIG. 22 is a 3-D diagram showing a geometrical relationship between the cube of viewed data 2201, a "look-at" point 2202 within the volume 2201, and a camera eye 2203. The diagram illustrates geometrical considerations related to camera movement with respect to the volume 2201. As described previously, an analyst adjusts a camera view 2203 to observe a data set from different positions, with different orientations, and/or to direct the camera view 2203 at different look-at points 2202. Optionally, the camera look-at point 2202 is fixed to an x-z plane and the analyst positions the look-at point 2202 anywhere within the base of the cube associated with the volume of data 2201.

The camera eye position 2203 is rotated about a vertical of the look-at point 2202 with any azimuth angle W, and rotated about the look-at point 2202 with an elevation angle E of between zero and ninety degrees. The analyst also selects a distance between the camera eye position 2203 and the look-at point 2202.

Near and far planes (see FIG. 5) are optionally determined in response to the distance between the camera eye 2203 and the look-at point 2202. The far plane is set such that, for example, the volume 2201 is never clipped, and the near plane is set at a fixed ratio of the far plane to maintain a fixed depth resolution.

When rendering (360) with shading effects, the analyst moves a light-source position in a similar manner as camera movement is selected. For example, a simulated light source is a point light source and/or a directional light source. Such sources provide contrast for the rendered topography of LC/MS data to assist study by an analyst. Such lighting techniques are known to one having ordinary skill in the graphical display arts.

Optionally, in addition to shading, various color schemes are applied to assist data interpretation. For example, a range of colors is optionally applied during rendering (360) to indicate the intensity of each displayed data point. Thus, color is used to give a sense of peak amplitude. The color of each point in a 3-D image is optionally a function of the intensity value at that point.

Mass, time, and/or intensity axes are optionally displayed to help the analyst maintain her sense of orientation while navigating through a 3-D visualization of a portion of a full set of data. The axes are optionally labeled with their respective axis name and data limits.

In one implementation, in response to selection of a point in a display, the three coordinates associated with that point are displayed. For example, a 2-D orthographic projection is used to display the coordinates in the lower left corner of the screen.

Figure 23:
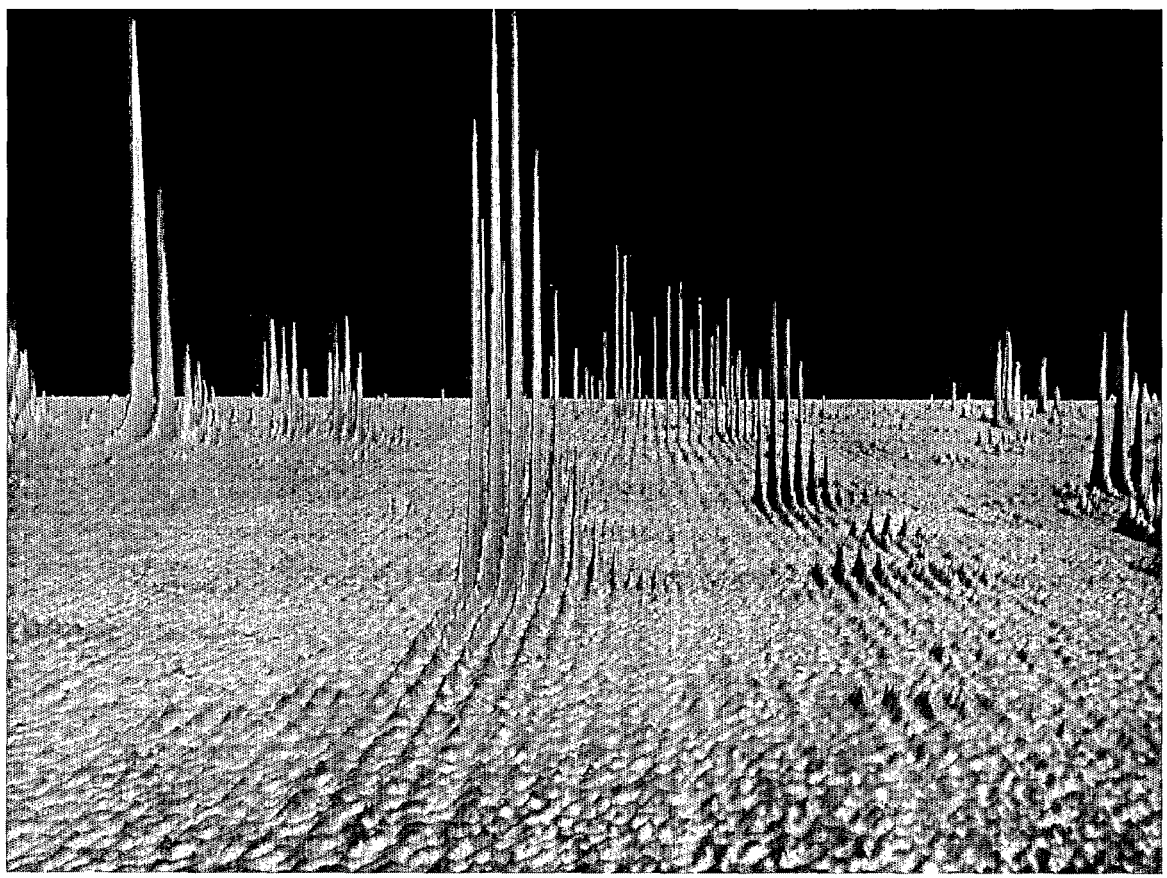
FIG. 23 is a screen shot of an image associated with animal-serum data, according to one embodiment of the invention.
Figure 24:
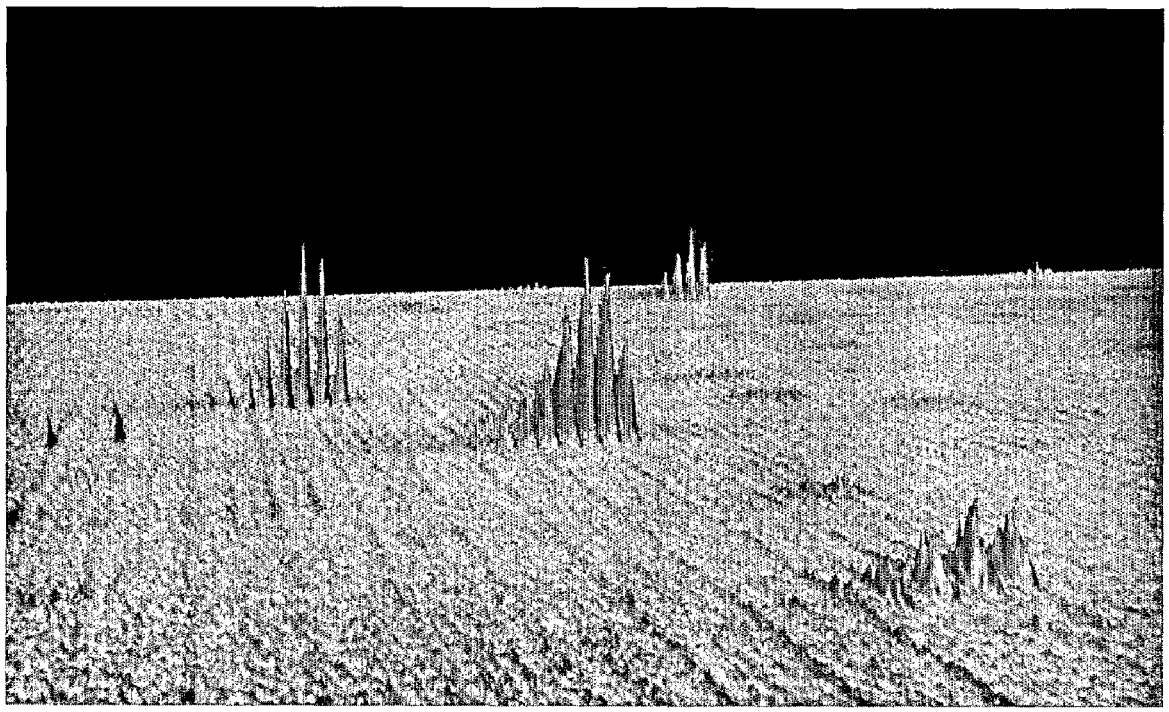
FIG. 24 is a screen shot of an image associated with the animal-serum data of FIG. 23.

Next referring to FIGS. 23 and 24, screen shots of visualizations are described for examples of different types of samples having data imaged under different view angles and different 3-D rendering conditions.

FIG. 23 is a screen shot of a displayed image associated with animal-serum data. The screen shot provides an example of a grey-scale 3-D visualization of the data. The foreground cluster of peaks are the isotopes of a triple charged fraction. The display conditions are shown in Table 1.

| | |
|---|---|
| Number of mass points | 354,305 |
| Number of time points | 2,669 |
| Number of grid levels | 11 |
| Mass tessellation | 346 |
| Time tessellation | 1,334 |
| Mass range (AMU) | 50-1,983.8 |
| Time range (minutes) | 0.06-130.01 |
| Mass scale | 1 |
| Time scale | 0.05 |
| Intensity scale | 0.05 |

FIG. 24 is another screen shot of a display of the data of FIG. 23, though with a different mass tessellation. The two center clusters are triple charged fractions, the small cluster in the foreground is a double-charged fraction, and the cluster near the horizon is also a double-charged fraction. The display conditions are shown in Table 2.

TABLE 2

| | |
|---|---|
| Number of mass points | 355,329 |
| Number of time points | 2,669 |
| Number of LOD levels | 10 |
| Mass tessellation | 694 |
| Time tessellation | 1,334 |
| Mass range (AMU) | 50-1,983.4 |
| Time range (minutes) | 0.06-130.01 |
| Mass scale | 1 |
| Time scale | 0.05 |
| Intensity scale | 0.05 |

Figure 25:
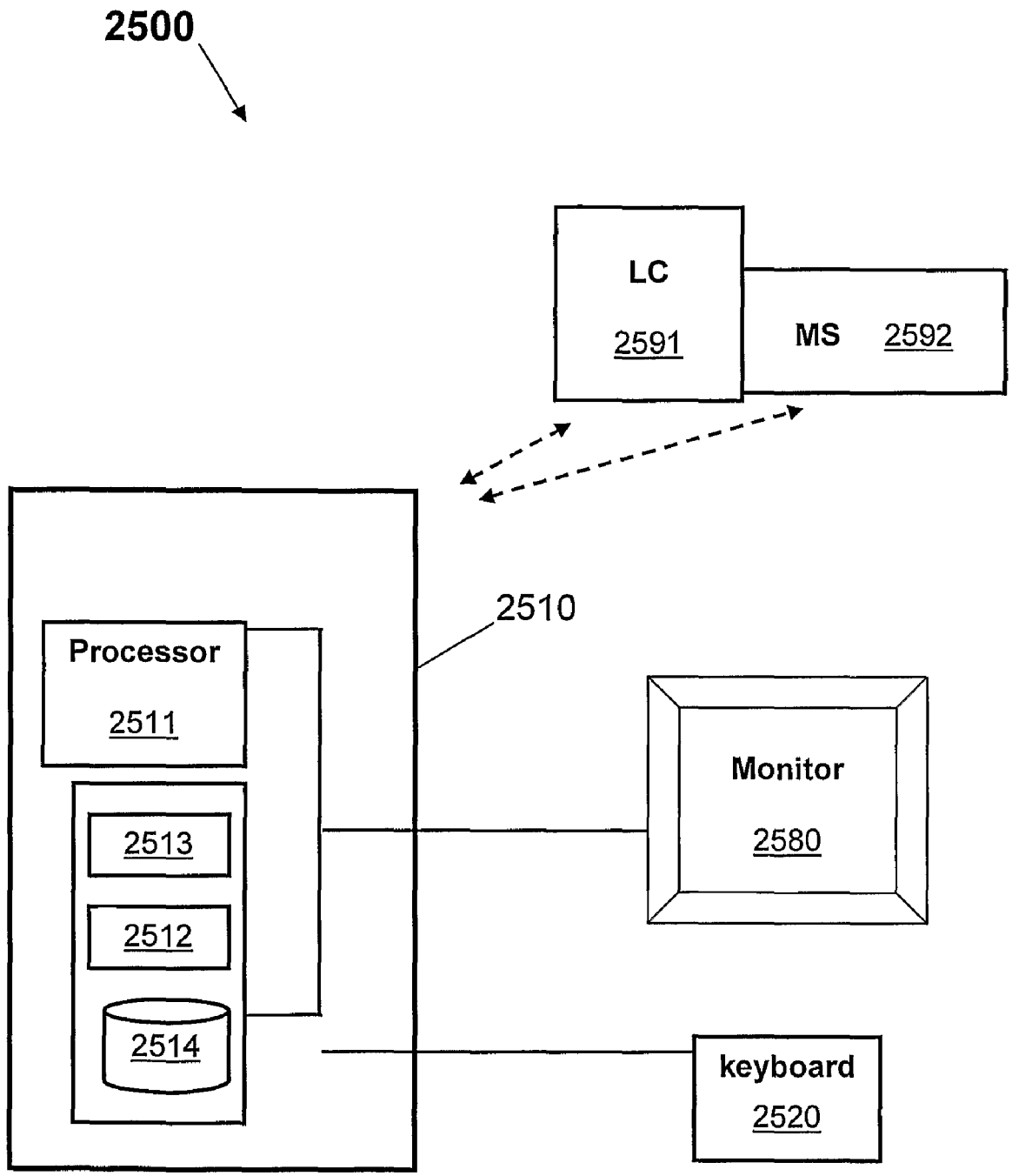
FIG. 25 is a block diagram of an analytical instrument, according to another embodiment of the invention.

Next referring to FIG. 25, as indicated above, some embodiments of the invention entail LC/MS instruments. FIG. 25 is a block diagram of an analytical instrument 2500, according to another embodiment of the invention. The instrument 2500 includes an LC module, 2591, a MS module 2592, a computer unit 2510, for control and analysis and in data communication with the modules 2591, 2592, a monitor 2580 that receives visualization instructions from the computer unit 2510, and a keyboard 2520 or other types of human interaction devices that supports analyst interaction with the computer unit 2510. The computer unit 2510 receives data from the modules 2591, 2592 and optionally provides control signals to the modules 2591, 2592.

The computer unit 2510 includes at least one processor 2511 and memory components, which include main memory 2513, such as dynamic random-access memory (DRAM), video RAM (VRAM) 2512, and a magnetic-medium hard-disk drive 2514. The main memory 2513 and/or the disk drive 2514 store instructions that, when executed, cause implementation of any one of the methods described herein, for example, the method 300. In alternative embodiments of an instrument, a computer unit is implemented via software, firmware, and/or hardware (e.g., as an application-specific integrated circuit.) The VRAM is optionally included in a dedicated graphics device, which may also optionally include a graphic processing unit (GPU). A GPU is optionally used, for example, to implement rendering of an image for display by the monitor 2580.

Some alternative computer units include, for example, one or more integrated circuits, such as microprocessors. A single integrated circuit or microprocessor in some alternative embodiments includes an instrument-control unit and other electronic portions of the system. In some embodiments, one or more microprocessors implement software that enables the functions of the control unit. In some embodiments, the software is designed to run on general-purpose equipment and/or specialized processors dedicated to the functionality described herein.

In one embodiment, the computer unit 2510 provides networked communication between the system and users located either local to the operating environment or remote from the operating environment.

In view of the description provided herein, various alternative embodiments will be apparent to one having ordinary skill in the data processing and presentation arts. For example, some alternative embodiments are based on different software languages and/or operating systems and/or hardware, and/or are applied to data derived from instruments other than LC/MS instruments. Accordingly, the detailed embodiments presented herein are illustrative, and are not intended to limit the scope of the invention to only the described embodiments.

Alternative embodiments include other features. One is the use of frustum culling to avoid sending to a GPU data that never reaches the screen. Another involves data storage in memory; instead of having just one data base from which all LOD levels take their data, one database per LOD level provides the resolution required by each level. This approach optionally improves memory updates, especially at higher levels.

Another alternative feature involves the overlay in 3-D of two or more LC/MS data sets with the purpose of comparison or difference identification. Alternately, the difference or some other operation between two or more LC/MS data sets are performed prior to the 3-D image rendering.

Another option is the use of a GPU for general computations, such as peak cluster identification. Other optional features include fixing of a viewpoint to specified mass and time coordinates and presentation of 2-D graphs that represent cuts of a 3-D visualization at selected locations.

Variations, modifications, and other implementations of what is described herein will occur to those of ordinary skill in the art without departing from the spirit and the scope of the invention as defined, in part, by the following claims.

What is claimed is:

1. A method for analyzing a chemical sample, comprising:
receiving, from a chemical analysis of the sample, data points each uniquely identified by a value pair of a retention-time and a m/z ratio and having an ion-intensity value;
compressing the received data points with preservation of substantially all data provided by the data points;
storing the compressed data points in a first memory;
generating, from the stored compressed data points, a plurality of nested data arrays, each array having a linearly graded time axis and a non-linearly graded mass axis, wherein each of the plurality of nested data arrays represents a portion of the data points at a different resolution level, a first of said plurality of nested data arrays at a first distance from a visualization viewpoint having a level of resolution providing more detail and greater density of data than a second of said plurality of nested data arrays at a second distance from the visualization viewpoint, said second distance being greater than the first distance;

storing the plurality of nested data arrays in the first memory or in a second memory;

rendering, in response to the visualization viewpoint, a current image from the stored plurality of nested data arrays; and displaying the rendered current image.

2. The method of claim 1, wherein compressing comprises eliminating at least some of the data points that have a zero ion-intensity value.

3. The method of claim 1, wherein compressing the received data points comprises associating a plurality of time values of the linearly graded time axis in one-to-one correspondence with a plurality of time indices, and associating a plurality of m/z values of the non-linearly graded mass axis in one-to-one correspondence with a plurality of mass indices, and addressing each data point having non-zero intensity value with a corresponding pair of the time and mass indices.

4. The method of claim 3, wherein generating the plurality of nested data arrays comprises generating at least one of the plurality of nested data arrays having a reduced density of data by removing a portion of the data points associated with each time index value, thereby preserving a time scale density and reducing a mass scale density.

5. The method of claim 3, storing all possible time values of the linearly graded time axis in an array that is addressed with the time indices, and storing mass values of the non-linearly graded mass axis in an array that is addressed with the mass indices.

6. The method of claim 1, wherein at least two of the plurality of nested data arrays are off-centered with respect to one another.

7. The method of claim 1, wherein the visualization viewpoint is associated with a pivot point that resides outside of all pairs of the retention-times and the m/z ratios of all ion-intensity values associated with the data points.

8. The method of claim 1, further comprising updating the generated plurality of nested data arrays in response to a change in position of the visualization viewpoint relative to the plurality of nested data arrays.

9. The method of claim 8, wherein updating comprises updating only if the change in position is greater than a threshold change.

10. The method of claim 1, wherein generating the plurality of nested data arrays comprises updating a portion of at least one of the arrays in response to the viewpoint moving greater than a threshold amount.

11. The method of claim 10, wherein rendering comprises, in response to the viewpoint approaching the plurality of nested data arrays, increasing a degree of detail and decreasing a field of view.

12. The method of claim 1, wherein rendering comprises rendering the image without a transition between contiguous image portions associated with adjacent array levels.

13. The method of claim 1, wherein the first memory comprises DRAM.

14. The method of claim 1, wherein the second memory is faster than the first memory, and the plurality of nested data arrays are stored in the second memory.

15. The method of claim 1, wherein the second memory resides in a graphical processing device, and wherein rendering comprises rendering by the graphical processing device.

16. The method of claim 1, wherein rendering comprises selecting a balance between a level of visible detail and a size of a field of view so that an amount of selected data for a particular view is approximately constant.

17. The method of claim 1, wherein rendering comprises associating a color pattern with intensity values, wherein the color pattern indicates relative intensities of at least some of the peaks.

18. The method of claim 1, wherein rendering comprises applying a selected lighting effect to the image.

19. The method of claim 1, wherein said rendered current image provides a visualization of at least a portion of the data points in three dimensions including retention-time, mass or m/z, and ion-intensity, and the method includes:

selecting a portion of the data points represented in the plurality of nested data arrays for rendering, wherein data points displayed are located inside a view frustum volume, the view frustum volume being a volume enclosed by a truncated projection pyramid determined by the visualization viewpoint, field of view angles and near and far planes.

20. The method of claim 1, wherein at least two of the plurality of nested data arrays each have different mass sampling densities and different mass resolution levels and each have a same time sampling density and same time resolution level.

* * * * *